(12) United States Patent
Strand et al.

(10) Patent No.: US 8,939,922 B2
(45) Date of Patent: Jan. 27, 2015

(54) STANDALONE SYSTEM FOR ASSISTING IN A LIFE-SAVING SITUATION

(75) Inventors: Geir Strand, Stavanger (NO); Helge Fossan, Stavanger (NO); Kenneth George Morallee, Orpington (GB); Helge Myklebust, Stavanger (NO); Rune Kristian Knutsen, Hundvag (NO)

(73) Assignee: Laerdal Medical AS, Stavanger (NO)

( * ) Notice: Subject to any disclaimer, the term of this patent is extended or adjusted under 35 U.S.C. 154(b) by 2144 days.

(21) Appl. No.: 11/816,270

(22) PCT Filed: Feb. 15, 2006

(86) PCT No.: PCT/NO2006/000061
§ 371 (c)(1),
(2), (4) Date: Jun. 7, 2010

(87) PCT Pub. No.: WO2006/088373
PCT Pub. Date: Aug. 24, 2006

(65) Prior Publication Data
US 2010/0256539 A1 Oct. 7, 2010

Related U.S. Application Data

(60) Provisional application No. 60/752,041, filed on Dec. 21, 2005.

(30) Foreign Application Priority Data

Feb. 15, 2005 (NO) .................................. 20050798

(51) Int. Cl.
*A61H 5/00* (2006.01)
*A61M 15/00* (2006.01)
(Continued)

(52) U.S. Cl.
CPC .......... *A61H 31/005* (2013.01); *A61H 2230/65* (2013.01); *A61M 2205/583* (2013.01);
(Continued)

(58) Field of Classification Search
USPC ...................... 434/262–275; 601/41; 600/587
See application file for complete search history.

(56) References Cited

U.S. PATENT DOCUMENTS 6,306,107 B1   10/2001  Myklebust et al. ........... 600/587
6,351,671 B1   2/2002   Myklebust et al. ............... 607/5
(Continued)

FOREIGN PATENT DOCUMENTS

DE   2551875 A1   5/1977
DE   2845436 A1   4/1980
(Continued)

OTHER PUBLICATIONS

Abella, Benjamin S. et al., "Quality of Cardiopulmonary Resuscitation During In-Hospital Cardiac Arrest," (Reprinted) JAMA. 2005; vol. 293, No. 3, pp. 305-310.
(Continued)

*Primary Examiner* — Timothy A Musselman
(74) *Attorney, Agent, or Firm* — Dorsey & Whitney LLP

(57) ABSTRACT

A system and a method is disclosed for monitoring parameters during cardiopulmonary resuscitation, including a compression measuring means, a ventilation measuring means and a processing means. If at least one of the measured values deviate from a respective reference range, the processing means provides an indication of the deviation. If more than one of the measured values deviate from a respective reference range, the deviations are prioritized with an indication being provided first to the deviation having a higher priority. The invention also regards a device for positioning on a patient's chest during cardiopulmonary resuscitation, which measures compression and which comprises a feedback module for providing a tactile output related to the measurements.

27 Claims, 10 Drawing Sheets

(51) Int. Cl.
  *A61H 31/00* (2006.01)
  *A61M 16/00* (2006.01)
  *A61B 5/08* (2006.01)
  *A61B 5/091* (2006.01)

(52) U.S. Cl.
  CPC  *A61M2016/0036* (2013.01); *A61H 2201/5084* (2013.01); *A61M 2230/65* (2013.01); *A61B 5/0816* (2013.01); *A61M 2205/582* (2013.01); *A61H 2201/5071* (2013.01); *A61B 5/091* (2013.01); *A61M 16/0078* (2013.01); *A61M 2205/581* (2013.01); *A61H 2230/40* (2013.01); *A61M 2230/50* (2013.01); *A61M 16/0084* (2013.01); *A61M 2016/0027* (2013.01); *A61M 2230/432* (2013.01); *A61M 15/0086* (2013.01); *A61H 31/007* (2013.01); *A61M 2230/63* (2013.01); *A61H 31/006* (2013.01); *A61H 2230/42* (2013.01)
  USPC ........................................................... 601/41

(56) References Cited

U.S. PATENT DOCUMENTS

| | | | |
|---|---|---|---|
| 6,390,996 B1 | 5/2002 | Halperin et al. | 601/41 |
| 6,727,419 B1 * | 4/2004 | Diaz | 84/484 |
| 7,976,312 B2 * | 7/2011 | Eggert et al. | 434/267 |
| 2002/0067336 A1 | 6/2002 | Wegmuller et al. | 345/156 |
| 2004/0082888 A1 | 4/2004 | Palazzolo et al. | 601/41 |
| 2004/0267324 A1 | 12/2004 | Geheb et al. | 607/5 |

FOREIGN PATENT DOCUMENTS

| | | |
|---|---|---|
| EP | 0555590 A2 | 12/1992 |
| EP | 1119385 A1 | 8/2001 |
| EP | 1079310 A2 | 10/2001 |
| EP | 1157717 A1 | 11/2001 |
| EP | 1578340 | 7/2004 |
| EP | 1491175 A1 | 12/2004 |
| EP | 1491176 A1 | 12/2004 |
| GB | 2344529 | 6/2000 |
| JP | 03-070573 | 3/1991 |
| WO | 00/27464 | 5/2000 |
| WO | 2006/088373 | 8/2006 |

OTHER PUBLICATIONS

American Heart Association, "Guidelines 2000 for Cardiopulmonary Resuscitation and Emergency Cardiovascular Care," Circulation. 2000; 102 (suppl. I): I-95-I-104.

Aufderheide, Tom P. et al., "Hyperventilation-Induced Hypotension During Cardiopulmonary Resuscitation," Circulation, 2004, pp. 1-6.

van Alem, Anouk P. et al., "Interruption of Cardiopulmonary Resuscitation With the Use of the Automated External Defibrillator in Out-of-Hospital Cardiac Arrest," Annals of Emergency Medicine. Oct. 2003; 42:4, pp. 449-457.

Wik, Lars et al., "Quality of Cardiopulmonary Resuscitation During Out-of-Hospital Cardiac Arrest," (Reprinted) JAMA. 2005; vol. 293, No. 3, pp. 299-304.

* cited by examiner

STANDALONE SYSTEM FOR ASSISTING IN A LIFE-SAVING SITUATION

CROSS-REFERENCE TO RELATED APPLICATIONS

This application is a national phase application of International Patent Application Serial No. PCT/NO2006/000061, filed Feb. 15, 2006, which application claims priority to U.S. Provisional Patent Application Ser. No. 60/752,041, filed Dec. 21, 2005, and to United Kingdom Patent Application Serial No. 0503834.4, filed Feb. 24, 2005, and to Norwegian Patent Application Serial No. 20050798, filed Feb. 15, 2005, all of which are hereby incorporated by reference.

TECHNICAL FIELD

This invention relates to a systems and devices designed to measure, record and provide feedback on the performance of cardiopulmonary resuscitation (CPR) as applied to victims of cardiac arrest or a manikin used for training purposes.

BACKGROUND OF THE INVENTION

Cardiopulmonary resuscitation (CPR) is a procedure performed as life-saving first aid in cases of a sudden cardiac arrest. The procedure comprises performing chest compressions and ventilation. Recent publications have pointed out numerous problems with how CPR is being conducted today by professionals.

Aufderheide et al showed in their publication "Hyperventilation-Induced Hypotension During Cardiopulmonary Resuscitation", Circulation. 2004; 109 that trained Emergency Medical Services (EMS) personnel had problems ventilating correctly. Even after re-training, the ventilation rate was still too high compared to the "Guidelines 2000 for Cardiopulmonary Resuscitation and Emergency Cardiovascular Care" published by The American Heart Association, in collaboration with International Liaison Committee on Resuscitation (herein after referred to as "the Guidelines").

Van Alem, Sanou and Koster pointed to another problem with performed CPR in "Interruption of Cardiopulmonary Resuscitation With the Use of the Automated External Defibrillator in Out-of-Hospital Cardiac Arrest", Annals of emergency medicine 42:4 (October 2003). Even trained EMS personnel that performed CPR conducted compressions or ventilations less than 50% of the time at the scene, i.e., hands-off time/inactivity time was too high.

Two articles in Journal of American Medical Association (JAMA) published Jan. 19, 2005, Vol 293, No. 3, "Quality of Cardiopulmonary Resuscitation During In-Hospital Cardiac Arrest" by Abella et. al. and "Quality of Cardiopulmonary Resuscitation During Out-of-Hospital Cardiac Arrest" by Wik et. al., conclude that hands off time was too high, the correct compression depth was not reached, compression rate was either too low or too high and that hyperventilation happened frequently.

Many CPR assist devices are known. U.S. Pat. No. 6,306,107, Myklebust et al, "System for Measuring and Using Parameters During Check Compression in a Life-Saving Situation or a Practice Situation and Also Application Thereof," describes such a device. This device does not consider ventilation, ventilation inactivity or compression inactivity.

Another description of a CPR device is described by Halperin et al in U.S. Pat. No. 6,390,996, "CPR Check Compression Monitor." This device only considers compression. Other, simpler CPR assist devices base their feedback on force and time. One such device is CPREzy from Medteq Innovations Pty. Ltd.

Some CPR assist devices are part of an Automatic External Defibrillator (AED) or a Defibrillator. One such device is part of AEDPlus from Zoll Medical Corporation. That device only considers compressions. Acquiring a new defibrillator with a CPR assist device might not be an option for Emergency Medical Systems (EMS) which already has a well functioning AED/Defibrillator system. Such EMS systems would rather consider a standalone solution for CPR measurement and feedback.

There are no prior art systems or devices that provide feedback on both compression and ventilation activity as well as on inactivity through the full procedure of CPR. These issues are believed to be very important in increasing CPR performance and thus survival rates.

Another problem related to known systems, such as for example the AEDplus from Zoll, is that they are relatively expensive, big, and complicated; so that lay rescuers will not keep them available at all times. Devices made for lay rescuers are described in EP1578340, which describes force sensitive devices giving sound signals for assisting the rescuer, and, more particularly, a device for placement between the hands of a person performing chest compression and the chest of a patient. Even more particularly, the device that is the subject of EP1578340 is designed to emit a sound when chest compression is performed with a force exceeding a pre-defined value and optionally also to emit a sound indicating the desirable rate of chest compression. This is obtained in an inexpensive and compact device which may be battery independent and thus always ready for use, or in the embodiment using a battery having a very low power consumption.

Practice has shown that sound signals in some cases may be difficult to hear, especially in some emergency situations. Also, there is in some instances a need for a more accurate basis for the feedback to the user. If, for example, the applied force is too strong, there is a risk of hurting the patient. Thus there is in such instances a need for an energy efficient and compact device for providing quality CPR feedback, where the feedback is provided in a way that is dependable and likely for the rescuer to receive under all possible situations.

SUMMARY OF THE INVENTION

An objective of the present invention is to provide a system and method for monitoring parameters during CPR, to enable a person to perform CPR correctly and efficiently by guiding him or her through the CPR based on the measurement and feedback of chosen parameters related to the CPR treatment, thus giving the patient a better treatment and greater chance of survival. Guiding is defined herein as corrective and directive feedback, where feedback may be in the form of tonal, verbal, tactile, vibration, lights and/or graphical prompts. Directive feedback may be reminders on how to perform specific steps of CPR.

A further object of the invention is to provide a device for providing feedback to the rescuer in order to improve the CPR treatment, the device being small, versatile, dependable and affordable.

The object of the invention is further to overcome the limitations of the referenced prior art.

These and other objects of the invention are obtained using a system and a device as described below and in the accompanying claims.

The feedback is in one embodiment provided by indications to the rescuer by means of tactile feedback to the rescuer's hand provided in an energy efficient way, e.g., to prolong battery life and thus the dependability of the device when stored without charging.

Important parameters that may be given feedback on based on the monitored signals from the system according to the invention include, but not are limited to, compression depth, compression rate, compression inactivity, incomplete release of compression, ventilation rate, ventilation tidal volume, inflation time of ventilation, and ventilation inactivity. In one embodiment of the invention, feedback is provided based mainly on monitoring compression.

The present invention may be stationed wherever many people gather, for example: airports, sporting arenas, shopping malls, subways, buses, etc. The invention is suitable for being used by both lay persons and trained persons. It may also be placed in EMS, police and/or firefighter vehicles, or be issued as a personal device for people giving basic life support (BLS).

The information measured by the present invention may also be recorded for later debriefing and/or transmitted to a medical emergency (communication) center and/or hospital. The transferred data might be used to further tailor hospital treatment provided to the patient that is submitted to hospital.

According to one embodiment, the system according to the invention for monitoring parameters during cardiopulmonary resuscitation, comprises a compression measuring means, a ventilation measuring means, a processing means connected to the compression measuring means and the ventilation measuring means and adapted for comparing the values from the compression and ventilation measuring means with respective reference ranges, and if at least one of the measured values deviate from the respective reference range, provide an indication of the deviation, wherein in the case of more than one measured value deviating from the respective reference ranges, the processing means is adapted to provide a sequence of indications in prioritized order.

According to a further embodiment, the system according to the invention comprises a feedback unit that provides the indication of a deviation in the form of an auditive, visual and/or tactile output.

According to one embodiment, the feedback unit comprises a coil wound around a central hole and a magnetic core moveably arranged in the central hole of the coil, the coil being connected to an electric power supply that is switched on and off in order to induce movement of the magnetic core.

According to a further embodiment, the ventilation measuring means measures ventilation rate, tidal volume and/or inflation time.

According to a further embodiment, the compression measuring means measures compression rate and/or compression depth.

According to a further embodiment, the compression measuring means and/or the ventilation measuring means and the processing means are integrated in a housing.

According to still a further embodiment, the compression measuring means, the feedback unit, and the processing means are integrated in a housing.

In a further embodiment, prioritization of the indication signals is performed by comparing the respective measurands corresponding to the deviating measured values with a priority list stored in the processing means.

In another aspect of the invention, a method for monitoring parameters during cardiopulmonary resuscitation in a life saving situation or in a practice situation, includes measuring compression, measuring ventilation, comparing the values from the compression and ventilation measurements with respective reference ranges, and, if at least one of the measured values deviate from the respective reference range, providing an indication of the deviation, and, in the case of more than one measured value deviating from the respective reference range, providing a sequence of indications in prioritized order.

In one embodiment the indication of a deviation is given in the form of an auditive, visual and/or tactile output from a feedback unit.

In one embodiment measuring ventilation comprises measuring ventilation rate, tidal volume and/or inflation time.

In a further embodiment, the ventilation measurements are performed in an airway adapter.

In one embodiment, compression comprises measuring compression rate and/or compression depth.

In one embodiment the compression measurements may be performed by a compression unit contacting the chest of a patient/manikin.

In one embodiment, the means for measuring compression and/or the means for measuring ventilation and the processing means are integrated in a housing.

In one embodiment of the invention, the means for measuring compression, the feedback unit and processing means are integrated in a housing.

In a further embodiment, prioritizing the indication signals is performed by comparing the respective measurands corresponding to the deviating measured values with a priority list.

The object of the invention may further be achieved by means of a device for positioning on a patient's chest during cardiopulmonary resuscitation, comprising compression measuring means measuring at least compression depth, processing means connected to the compression measuring means, adapted for comparing the values from the compression measuring means with a reference range, and if the measured values fall within the reference range, provide an indication signal, a feedback unit connected to the processing means for providing a tactile output related to the indication signal from the processing means.

In a further embodiment, the feedback unit is arranged off center of the device.

In still a further embodiment, the device comprises a cover, and there is provided a recess in the cover directly above the feedback unit.

In one embodiment of the invention, the device comprises connection means for connecting to other measuring means such as ventilation measuring means.

In another embodiment of the invention, the compression measuring means measures compression rate.

BRIEF DESCRIPTION OF THE DRAWINGS

The following will explain the invention in more detail, with reference to the accompanying drawings illustrating the invention by way of examples, in which.

DETAILED DESCRIPTION OF PREFERRED EMBODIMENTS

Figure 1:
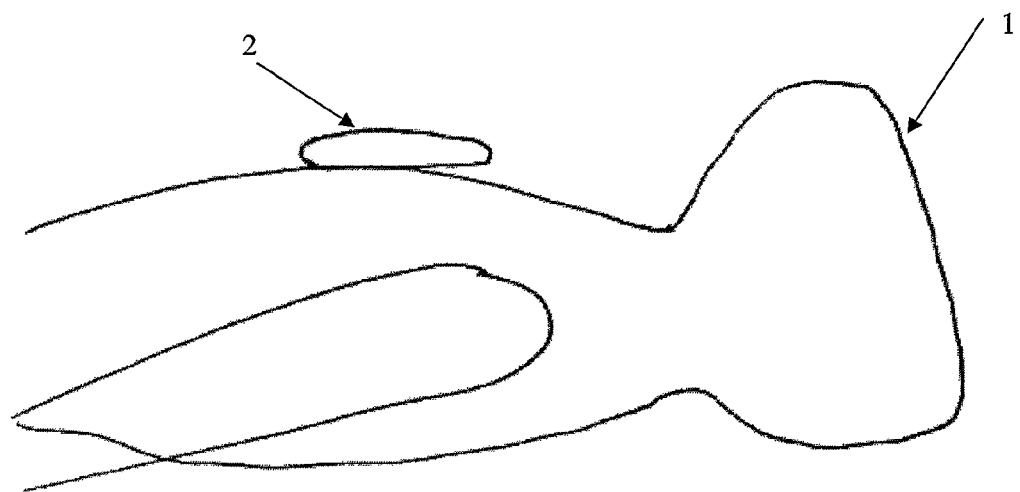
FIG. 1 schematically shows a person with a compression unit in accordance with an embodiment of the present invention.

FIG. 1 shows a patient 1 with a compression unit 2 attached to his/her chest. The unit 2 may be attached using adhesive tape. When a rescuer performs compressions on the patient's chest, the rescuer places his hand on top of the unit 2. The unit 2 will therefore travel the same distance as the chest is compressed. A movement sensor, including or connected to a calculation means, located inside the compression unit will detect the distance/depth. The movement sensor may be an accelerometer, but other solutions may be employed such as use of a gyro or distance measurements from a reference point or by triangulation. In case of an accelerometer, in order to find the depth, the signal from the sensor will have to be filtered and double-integrated, as is well know in the art. An additional force sensitive unit, in its most simple form just a force activated switch, will also be part of the unit. This force sensitive unit will be activated each time the rescuer performs a compression, and will therefore define the compression/integration time window/interval. This reduces the incidence of false positive compression detection. By having a force sensor instead of a force-activated switch, possible future changes in the CPR protocol/guidelines from depth to a force compression measure, or a combination thereof, may be facilitated. In one embodiment the compression unit may be arranged with a force transducer instead of a movement sensor. According to one embodiment of the invention, the compression unit 2 comprises a tactile feedback unit for providing tactile indications regarding the distance/depth measurement.

Figure 2:
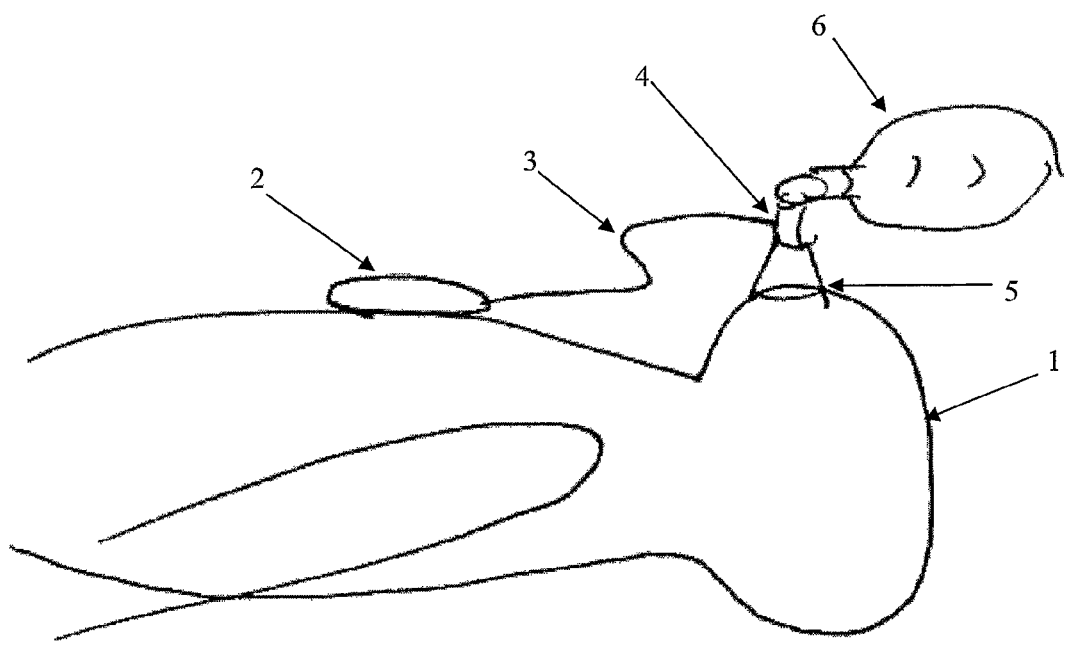
FIG. 2 schematically shows a person with a compression and airway adapter in accordance with an embodiment of the present invention.

FIG. 2 shows a patient 1 with the compression unit 2 attached to his/her chest. In addition to what is described about the compression unit in FIG. 1, the compression unit is connected either via a hose or electrical wire 3 to an airway adapter 4 that is placed between a mask or ET-tube 5 and a ventilation bag or ventilator 6.

In one embodiment, the airway adapter has a ventilation-measuring means of some type known in the art. One solution is to have a restriction in the airway, and measure the pressure drop over this restriction. The pressure sensor(s) may in this case be placed in the compression unit 2 or in/by the airway adapter 4. The flow can then be calculated inasmuch as it is square-root proportional to the pressure drop. the ventilation volume is found by integrating the flow.

Alternative ventilation-measuring means may be constituted by means other than differential pressure monitoring, such as monitoring temperature fluctuations in the air ways, which indicate whether the air is coming in or out of the person, a single pressure transducer, which measure the airway pressure inside the airway adapter 4 thus allowing detection of ventilation events and associated pressure profiles, or small turbines, all positioned in the airway. Alternatively, or in addition, impedance measurements of the chest for indicating the air volume in the lungs may be used, as described in the next section.

Other setups of the system may also be viable. The ventilation-measuring means may, for example, be integrated into the mask, and there may or may not be a ventilation bag. Instead the rescuer can use his/her mouth to ventilate the patient.

In addition or instead of flow measurements, end-tidal $CO_2$ (ETCO2) measurements may also be implemented. ETCO2 may be used as an indicator as to how good the treatment is, and thus if the CPR can be improved.

Advanced Life Support (ALS) personnel may intubate a cardiac arrest victim and perform compressions and ventilations at the same time. As the compressions will compress the lungs thus pushing air out of them, compressions may influence the ventilation measurements. Low pass filtering or adaptive filtering of the ventilation measurements may therefore be necessary. Adaptive filtering may use any single or combination of force, acceleration, velocity and/or depth as additional inputs, as they all relate to compression activity. How to do this is per se known to a person skilled in the art of signal processing.

Figure 3:
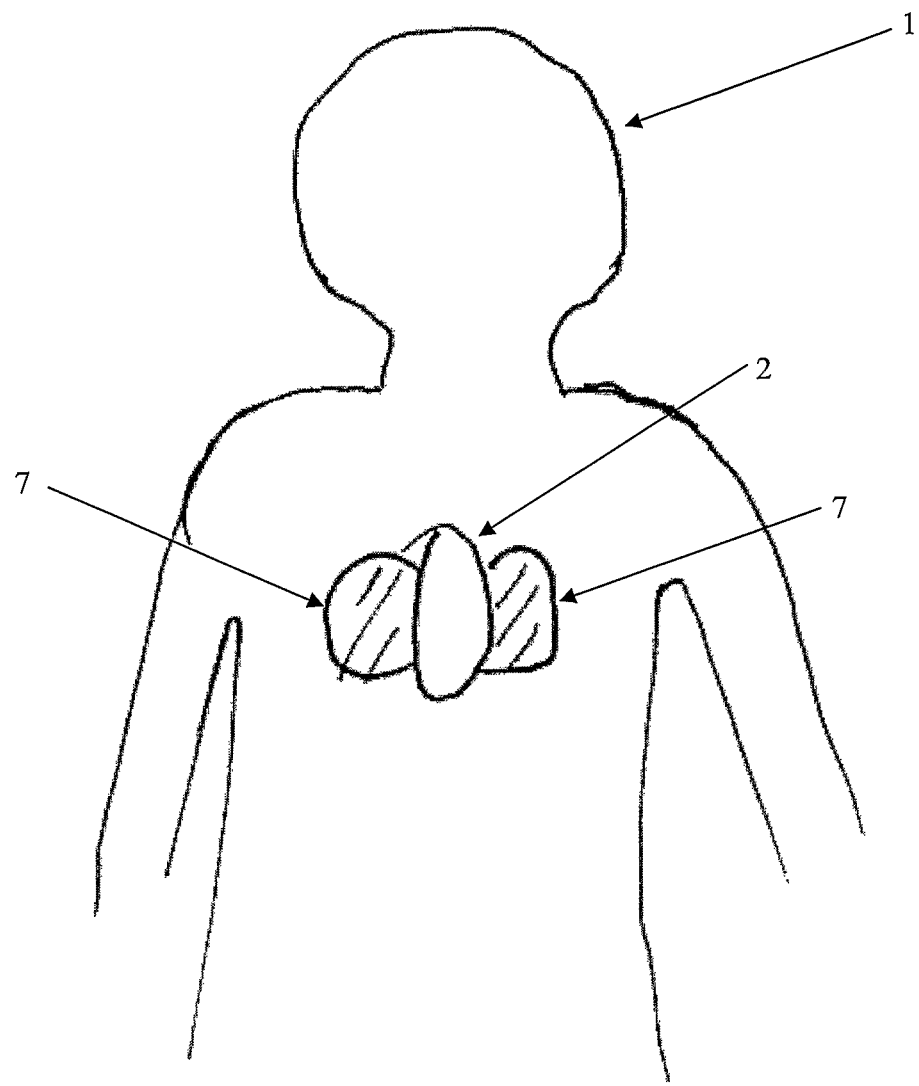
FIG. 3 schematically shows a person with a compression- and ventilation-unit having additional electrodes for implementation of the invention.

FIG. 3 shows a patient 1 with the compression unit 2 that, in addition to the abovementioned functionality, also has electrodes 7 attached to each side of the unit. These can be used to measure the impedance of the patients' thorax. The impedance of the thorax is normally measured by supplying an approximately constant alternating current between the electrodes and at the same time measuring the alternating voltage between the electrodes. It is also possible to apply an approximately constant alternating voltage between the electrodes and at the same time measuring the alternating current flowing between the electrodes. The electrodes may need to be placed in close proximity of the compression unit as well as be small in size as defibrillation electrodes might also be placed on the patient. Due to close proximity of the electrodes and their relatively small size, the preferred frequency to measure impedance may be higher than what typically is used; frequencies between 0.1 kHz to 500 kHz or even higher may be used depending on the electrode size. When the lungs are inflated the impedance of the thorax increases (path between electrodes increase), enabling the unit to detect if air actually got into the lungs. The impedance measurements per se are well known from other/similar applications and will not be discussed in any further detail here. Filtering may also be applied (to remove compression activity), as described in relation to FIG. 2.

The system according to the invention comprises a processing means of some type, for example, a microprocessor, microcontroller or some kind of programmable logic unit (CPLD or FPGA). The processing means may be integrated in the compression unit 2 or in the ventilation measuring means, or may be a separate unit. The processing means is preferably provided with rewriteable means, like flash memory for updating the programming and the predetermined set of preferred activities from which the deviations are found. The ability to update the processing means will be an advantage as "the Guidelines" are updated regularly.

Figure 4:
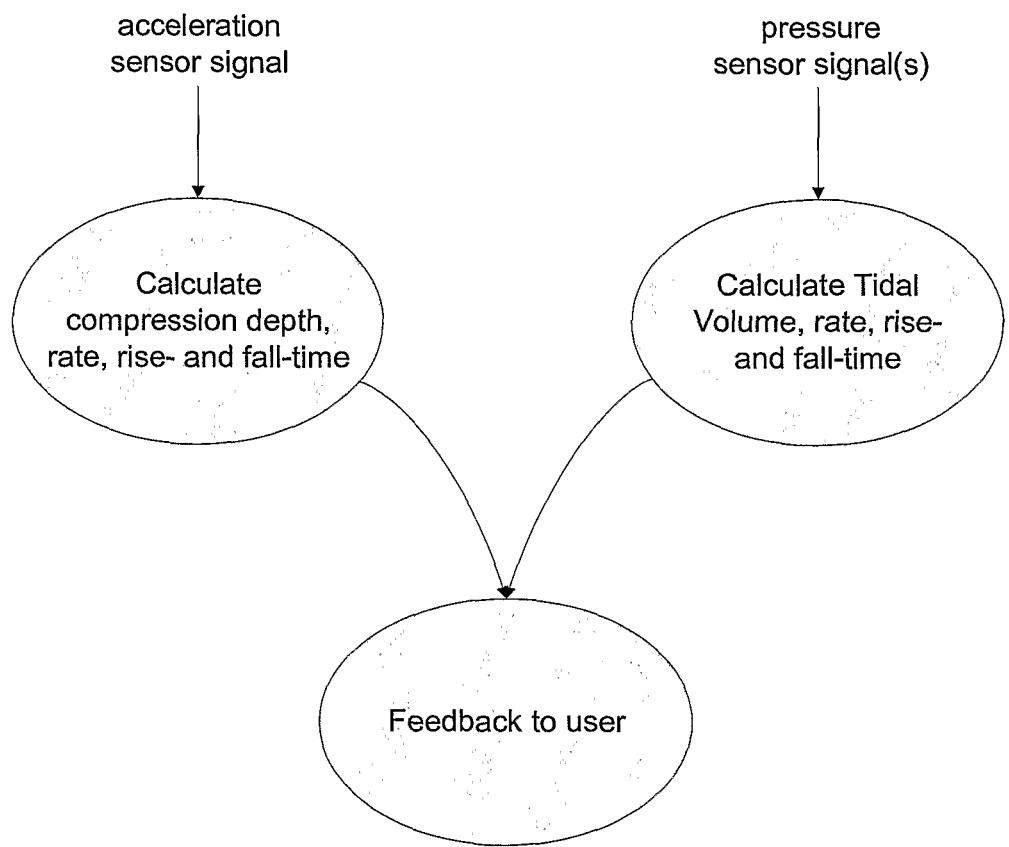
FIG. 4 is a flow diagram illustrating a generalized flow of information in the processing means in accordance with an embodiment of the present invention.

The processing means will be responsible for collecting information from sensors/measuring means, processing the individual signals, and deciding what kind of feedback to give the rescuer. This process is summarized in FIG. 4. If more than one parameter needs to be corrected, the processing means may include a priority process so that it selects giving feedback about the most critical parameter(s) first based on a priority list. A priority list is stored in the processing means, and may be a standard list, e.g., one mentioned in "the Guidelines", or may be defined by the user or the manufacturer according to the specific use of the system.

The system according to the invention is further arranged with some kind of feedback actuator 13, for example comprised in the compression unit 2. Since the rescuer usually has enough on his/her mind, feedback may preferably be given by means of voice prompts. This may, however, depend on the intended use of the equipment, as voice prompts in some cases, such as in crowded areas may be misinterpreted by bystanders or may be drowned out by noise. In such cases, tonal, visual, tactile or vibration feedback signals (e.g., beepers, blinking LEDs, solenoids or vibration motors) may be used. Different configurations may be used. In one example, a beeper is used to give compression rate feedback, either in the form of a corrective metronome indicating the correct rate when the rescuer is outside the correct rate range/window and being silent when the rescuer is within the correct rate range/window, or a directive metronome which indicates the desired rate continuously. Vibration of the device or a tap in the hand occurs when the compression depth is sufficient and a LED blinks to provide directive feedback on ventilation rate. In another example, a stack of LEDs is used to show compression depth, each LED illuminating when a certain depth is reached. Thus one embodiment can use combination of verbal, tonal, visual, vibration and/or tactile feedback. The compression unit 2, the ventilation measuring means and/or the processing means, may also be connected to a separate feedback unit, which may be a part of any other display/feedback equipment for use on that location.

In addition, a recording means may be available wherein the measured information, e.g., raw sensor data and/or events and feedback delivered may be stored for later retrieval. The measured information may be stored in the processing means 12 or in a separate storage device, e.g., a flash type memory (card) 14. The recording function may be used for tailoring training according to each rescuers need, and may be part of a continuous quality improvement (CQI) program. The recording function may be implemented in the device or be transferred to a computer or other devices, e.g., by radio communication. One possibility is that the device is adapted to communicate with a defibrillator thus constituting a part of a larger set of life saving equipment. In such a situation, some of the feedback to the user may be given from the AED/defibrillator, although measured by the compression unit 2. Such communication might be in the form of wireless or wired communication.

In one embodiment of the system according to the invention, all of the components are implemented in the compression unit 2 comprising energy supply and processing power sufficient to be used alone, preferably with input means and/or connection means for receiving ventilation data, either electronically as measurement signals, or as pressure transferred through one or more suitable tubes or other suitable physical transferal of physical properties for direct measurement in the compression unit 2. Also the compression unit 2 may comprise electrodes, or connection/coupling for electrodes, for impedance measurements.

Figure 5:
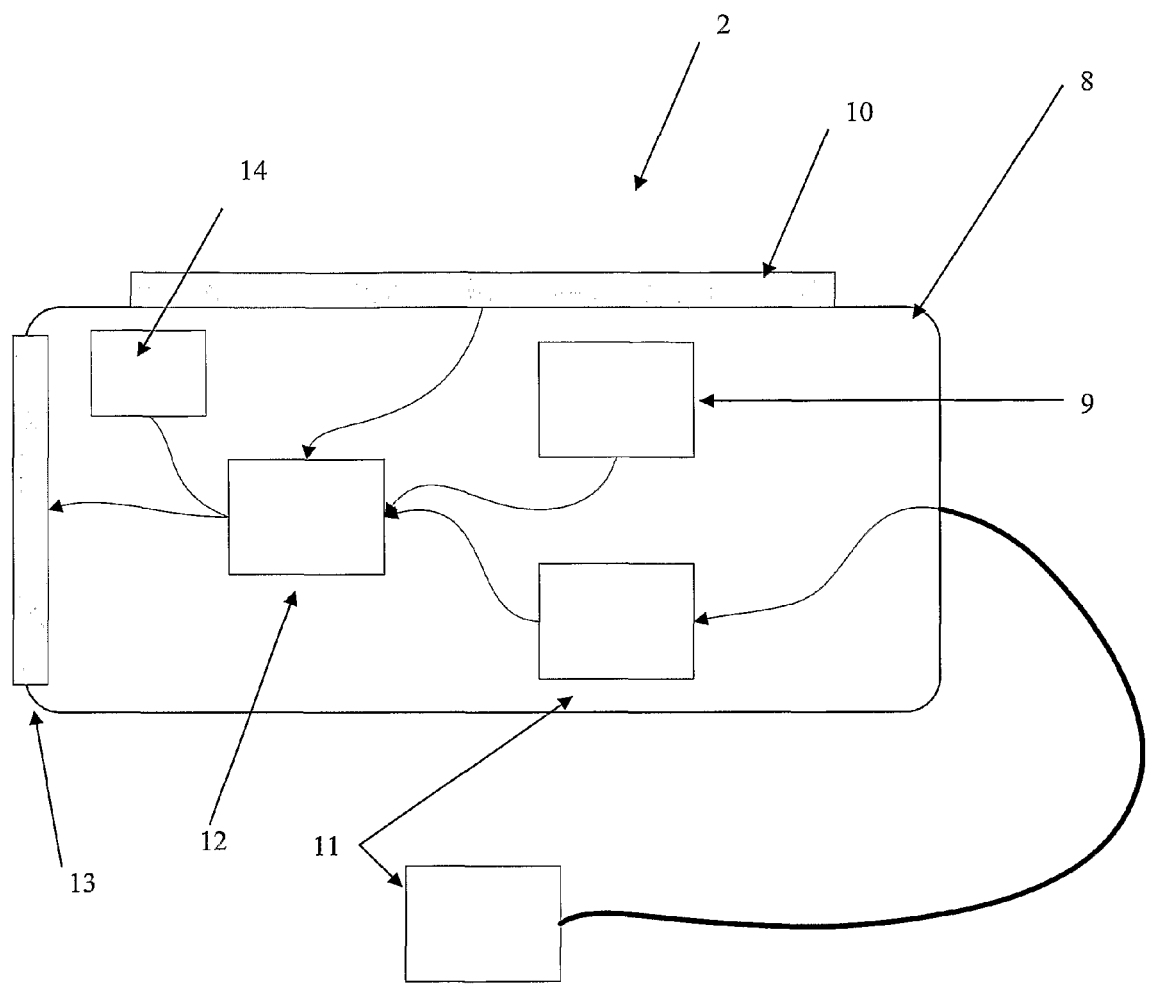
FIG. 5 is a schematic block diagram of system components for a device in accordance with an embodiment of the present invention.

Such an embodiment is shown in FIG. 5. Most of the components are inside the housing 8, such as the processing means 12, a movement sensor 9, and ventilation measuring means 11 (this may alternatively be arranged outside the housing and the signal transferred to the electronics inside the housing 8). The force sensitive unit 10 is shown on the outside of the housing, but other solutions may also be viable. One other solution is to have a housing that flexes, that is, the distance between the outer housing and the inner components decreases slightly when a force is applied. It will therefore be possible from inside the housing to measure the force. The feedback actuator 13 may be arranged outside the housing with a connection to the processing means 12 through the walls of the housing. In case of voice feedback through a speaker, the speaker may reside inside the compression unit, the compression unit being provided with a slot in the housing 8 to allow the sound out of the device. In case of tactile feedback, the feedback actuator will preferably be integrated in the housing.

Figure 6:
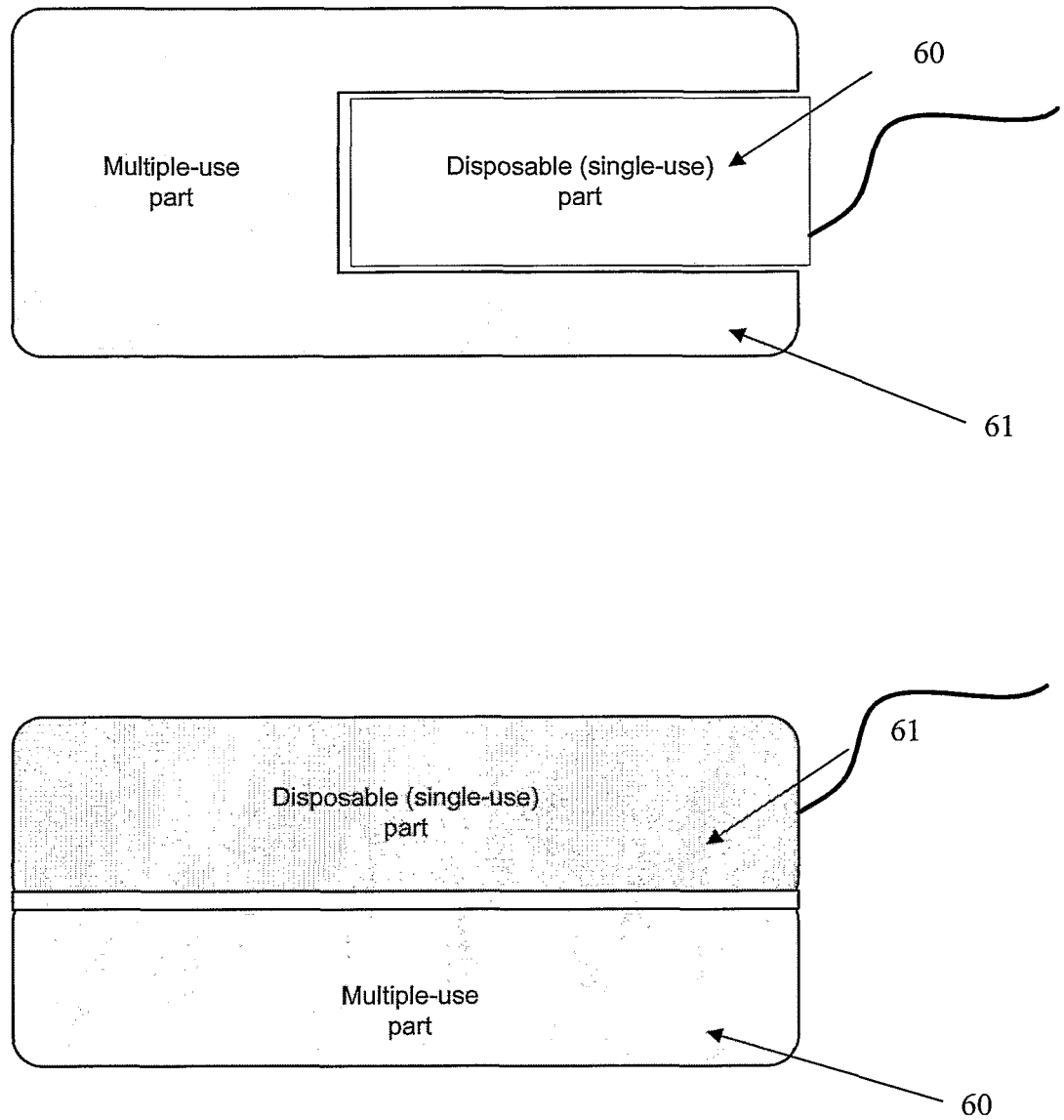
FIG. 6 is a side view of an alternative embodiments of the device in accordance with an embodiment of the present invention.

Two alternative embodiments of the system are presented in FIG. 6. These alternative embodiments comprise two modules; one for single-use (disposable) 61 and one for multiple-use 60. The reason for this two module approach is that parts being in contact with the patient should be disposed of for hygienic reasons. It will also function as a way to renew the energy supply. There might be both electrical and mechanically interconnections between these modules. Typically the disposable module 61 contains energy supply, feedback means, and connections to the external flow-measuring means. The multiple-use module 60 typically contains the processing means, the movement sensor and force sensitive unit.

Figure 7:
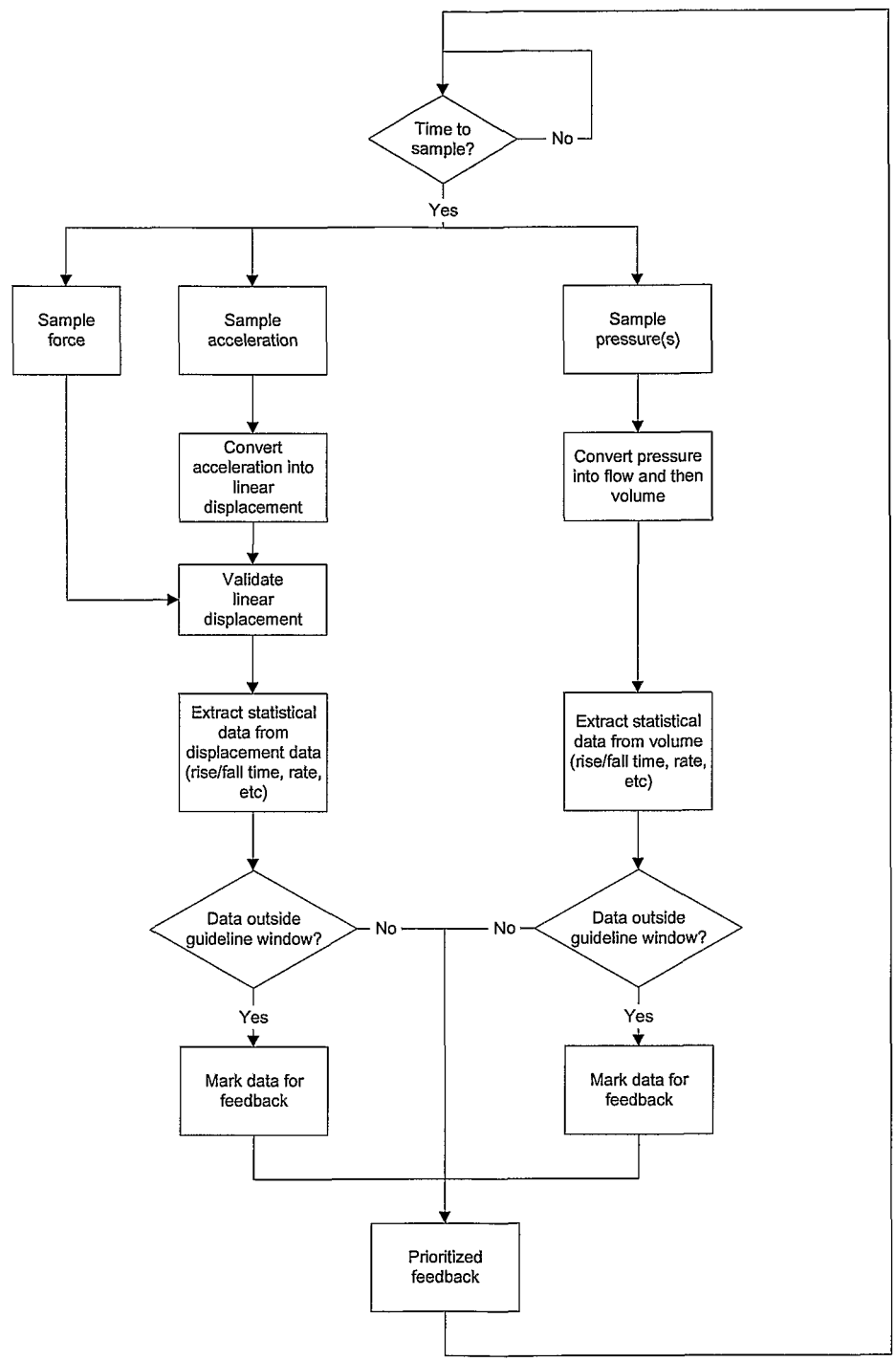
FIG. 7 is a flow chart illustrating a method for performing CPR in accordance with an embodiment of the present invention.

FIG. 7 shows a flow chart that illustrates one possible signal flow in a preferred embodiment of the invention. This embodiment comprises means for measuring compression and ventilation, which means that it may be necessary to provide different signals related to each necessary feedback. At certain intervals all signals of interest, in this case the acceleration signal as well as the force sensor to monitor compression and the pressure signal to monitor ventilation, are collected/sampled, and then separately treated in order to produce parameters of interest, such as compression depth, compression rate, compression inactivity, incomplete release, ventilation rate, tidal volume, inflation time and ventilation inactivity.

In the illustrated example, the acceleration data is converted into linear displacement (depth). The force sensitive unit is employed to validate the depth, i.e., the depth is not considered when the force is below a certain threshold. From the validated depth statistical data is extracted, such as rise/fall time, compression rate, etc. The sampled pressure signals are converted into flow and then into ventilation volume, and statistical data such as rise/fall time, ventilation rate etc is extracted. If any of the statistical data is outside predetermined limits the data is marked for feedback to the user.

The predetermined limits are stored values which may be based on statistical models or previous samples recorded from earlier use, e.g., corresponding to known deviations from preferred CPR procedures as described in "the Guidelines" as mentioned above.

Thus each main loop of the flow chart (compression or ventilation) then decides if any feedback is needed on a parameter, mark this as the feedback to be given. A common (voice) feedback module then decides which parameter should be given feedback on, based on a priority list. The priority list is in this case stored in the feedback module. In one embodiment, the feedback module is a programmed module integrated in the processing means 12. These loops continue to operate until the device or system according to the invention is switched off, or possibly as long as the force switch or sensor detects activity over a certain level.

There are instances wherein only one of these loops may be suitable, e.g., a simpler device for used by lay-persons. The system described in FIG. 7 is, however, preferable both for its flexibility in different situations and for the quality of the output. Also, it is possible to base these loops on other parameters, by combining the parameters or add more loops, e.g., from the force sensor, within the scope of this invention.

Figure 8:
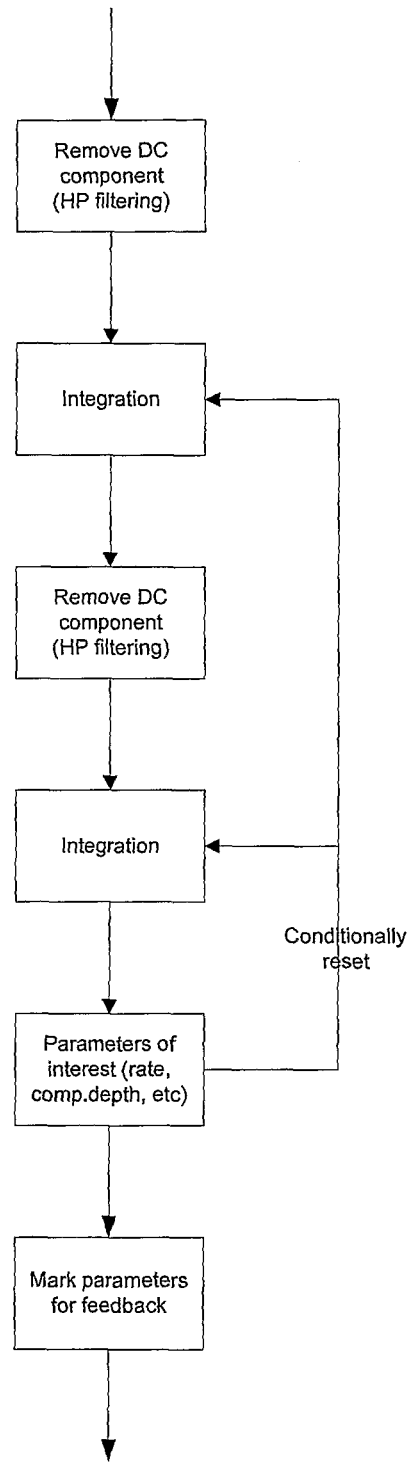
FIG. 8 is a flow chart illustrating for providing feedback using an accelerometer output in accordance with an embodiment of the present invention.

FIG. 8 shows more details regarding one possible acceleration signal processing flow. Most of this signal processing can be done either in the analog domain (before digitalization) or in the digital domain, however here we will only discuss all processing done in the digital domain. First of all the acceleration signals needs to have its DC component removed. This can be accomplished by using a high-pass filter that is either an IIR- or FIR-filter type. A notch filter may also be used. Using a FIR-filter of length M results in $$a_{filt}[n] = \Sigma_{i=0}^{M} c_i \cdot a[n-i]$$

where a is the raw acceleration signal and $a_{filt}$ the filtered acceleration signal.

The filtered acceleration signal is then numerically integrated, $$v_{raw}[n] = C \cdot (a_{filt}[n] + a_{filt}[n-1]) + v_{raw}[n-1]$$

where C is half the sampling interval (T/2). This raw integrated signal is then high-pass filtered with a filter that may be similar to the first filter, $$v_{filt}[n] = \Sigma_{i=0}^{M} c_i \cdot v_{raw}[n-i]$$

This filtered signal is again numerically integrated, $$s[n] = C \cdot (v_{filt}[n] + v_{filt}[n-1]) + s[n-1]$$

where s is then used as the depth. One possible solution to keep drift in the depth signal to a minimum is to keep the integration variables at zero for as long as the force sensor, either a switch or a real force sensor, is not activated. Another solution is to zero out the integrations (both $v_{raw}$ and s) every time the depth has a turning point (first derivative approximately zero (positive to negative), second derivative negative) close to zero depth. After this other parameters may be extracted from s. For example compression depth (check for maximum value between two resets) and compression rate (time between two maximum values).

When a CPR error is detected it is forwarded to a feedback software module using a slightly modified Last-In First-Out (LIFO) buffer, that is, it is always the most recent CPR error which is considered for feedback. Errors in the buffer which is more than A seconds old will be deleted. After a verbal feedback has been delivered, the next feedback is considered after typically B seconds. A and B are configurable parameters, typically in the range of 2-6 seconds.

One way to do the prioritizing of feedback is by sorting all CPR errors that occurred at a certain time step according to their priority, and only placing the CPR error with the highest priority into the LIFO buffer. In that way, the feedback software module only has to verify that no other feedback message is given before executing the feedback warning. This ensures that the most critical error is considered for feedback first.

Another method is to place every CPR error into the LIFO buffer, and perform the prioritizing in the feedback software module. This enables more customization, i.e., different errors may reside in the LIFO buffer for longer periods of time than others, depending on the criticality of the error.

Details of one embodiment of a tactile unit included in the device 2 illustrated in FIGS. 1 and 2 are shown in FIGS. 9 to 15. The rescuer positions his or her hand on the device 2 and performs CPR. According to a preferred embodiment of the device, according to the invention illustrated in FIG. 9, the device provides a feedback to direct the rescuer to deliver a desired compression depth, for example by providing a small tap on the rescuers hand when the compression has reached sufficient depth in each correctly performed compression.

Figure 9:
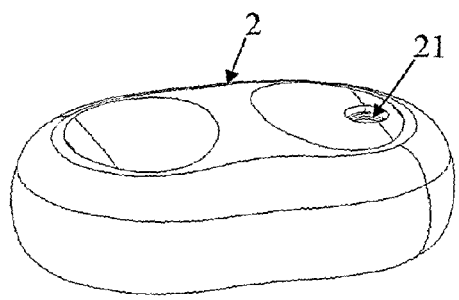
FIG. 9 is an isometric view of a tactile feedback device in accordance with an embodiment of the present invention.
Figure 11:
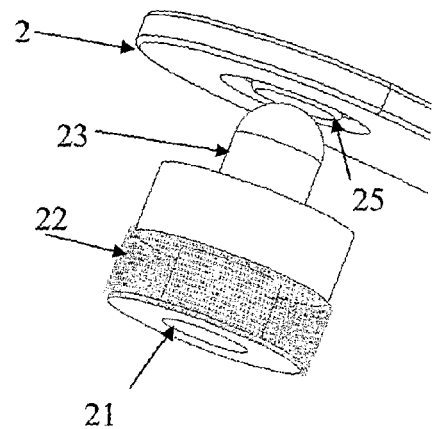
FIG. 11 illustrates the position of the feedback unit inside the device of FIG. 9 in accordance with an embodiment of the present invention.
Figure 10A:
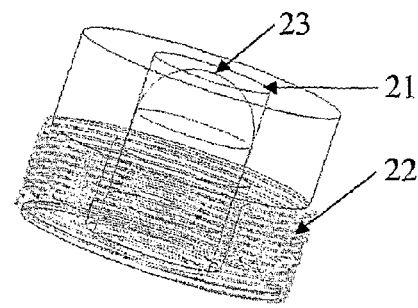
FIGS. 10a-10c illustrate different operating positions of the feedback unit of FIG. 9 in accordance with an embodiment of the present invention.
Figure 10B:
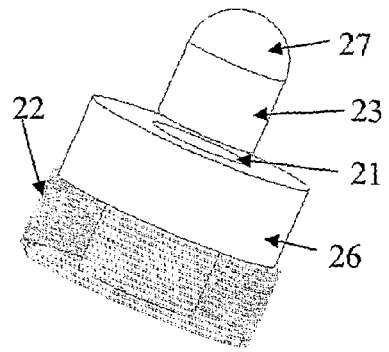

Referring to FIGS. 9, 10 and 11, the feedback unit comprises a coil 22, which is positioned inside the device 2, preferably off-centered/in one end section of the device, the coil having a central hole 21 adapted for insertion of a core 23 of a magnetic material positioned in the center (FIG. 10a). The direction of the magnetic field of the core and the coil when a current is applied to it is chosen so as to move the core out of the central hole 21 (FIG. 10b). This will be described in more detail below.

As is seen from FIGS. 10a and 10b, a wire is wound around a coil former 26 creating a coil 22, which also secures the central position of the coil. The core 23 may be equipped with a rounded end section 27 of a chosen material to make the contact with the user more tactile and easy to detect. The core 23 may be made of any desired material.

Figure 10C:
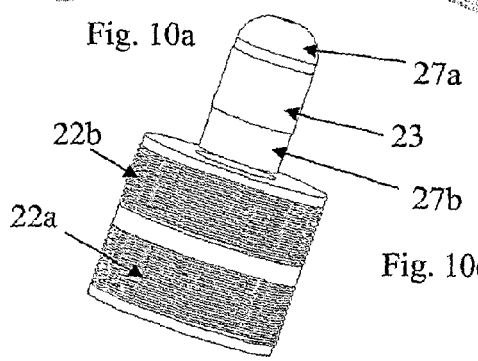

Making at least one end section of the core 23 of iron provides the further advantage that the field lines from the magnet are changed into a radial distribution in the iron. This concentrates the magnetic field in a smaller region outside the magnet of the core, gives the field lines a more preferred direction/distribution in the end sections, and thus provides a more forceful interaction with the electromagnetic field from the coil. This will thus increase the efficiency. A further improvement of this concept is illustrated in FIG. 10c, wherein iron parts 27a,27b are added on both ends of the magnet. In FIG. 10c, an additional coil 22b is also added, which can be controlled separately or simultaneously to the first coil 22a, to make a more uniform magnetic field to interact with the magnetic core. The current flowing in the two coils 22a, 22b may, for example, have opposite directions to impose attraction to one end of the core, and repulsion of the other end.

As is evident from FIG. 9 the feedback actuator is preferably placed off center in the sensor, as tests have shown that it is unpleasant to get a snap in the middle of the hand when performing CPR for a long periods of time.

The top cover of the device 2 is in the illustrated embodiment made of a soft and/or flexible material, and there is provided a recess in the cover in an area around the impact point of the feedback actuator such that this area is hollowed (FIG. 3). When the magnet core hits the cover, only a limited part of the cover is moving, thus making the snap more effective. Alternatively some of the material can be removed at the impact point, but this can result in an unpleasant and hard snap to the hand. The device 2 has preferably a rubber skin 25 or similar covering the hole 21 and magnetic core 23, so that the core 23 makes a tactile tap through the skin 25 when it is triggered.

The principle of this circuitry is well know as the principle of, e.g., an electromagnetic cannon. The tactile feedback unit will be explained schematically with reference to FIGS. 12a, 12b, 13a, and 13b, while the associated circuitry is described in FIGS. 14 and 15. The main feature of this solution is the simple structure and efficiency of the feedback compared to the energy consumption related to it, as it provides a large momentum to the core as a response to a relatively low energy pulse. In the illustrated example the coil has a winding direction being counter clockwise (as seen from above) and the core 23 of magnetic material placed with the positive pole down toward the bottom of the device, and the negative pole aimed upward. When the device is not active the core rests in a lowered position on the device housing 24 (see FIG. 13b).

Figure 12A:
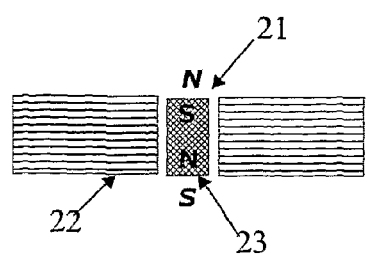
FIGS. 12a 12b are schematic illustrations of the feedback unit in accordance with an embodiment of the present invention.
Figure 12B:
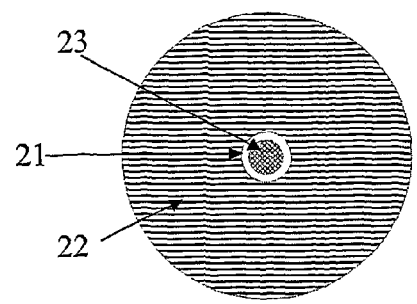

In FIG. 12a the feedback unit utilizes magnetic forces of an electric coil 22 and a powerful permanent magnet 23 constituting the core positioned in the center. The feedback unit will expel the magnet 23 from the hole 21 of the coil when a magnetic field is created in this coil hole. The magnetic field is created by a current through the coil windings.

When a current is applied to the coil 22 a magnetic field is created having the same direction as the magnet 23. This makes the magnet accelerate and move out of the magnetic field as seen in FIG. 13b up toward the rescuers hand.

Figure 13A:
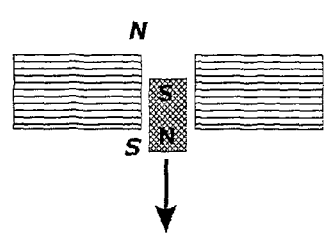
FIGS. 13a-13b are schematic illustrations showing operation of the feedback unit in accordance with an embodiment of the present invention.
Figure 13B:
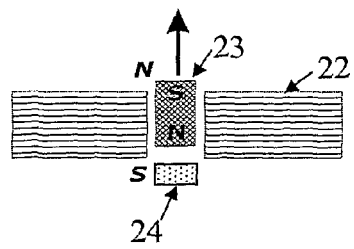

If the permanent magnet 23 and coil 22 are oriented as shown in FIGS. 13a and 13b and the current through the coil generates a field of the direction shown by N and S for the coil, the magnet will be "shot" out of the coil. The direction depends on how the permanent magnet is offset before the application of the current. In fact if it was possible to perfectly center the magnet it would remain motionless. However this is not achievable in practice, and in this case it is convenient to provide a support 24 for the magnet 23 slightly out of center in the upward direction, so that the direction of the magnets movement is predetermined. The force on the magnet will remain fairly stable from approximately half way up the coil until the magnet leaves the gap (if the field created by the coil remains constant) Above the gap the forces diminish rapidly and the magnetic forces tends to apply rotation to the magnet.

Since the magnet is accelerated out of the coil, it is energy efficient to apply a field in the coil for just a short time, e.g., just enough to provide the magnet with sufficient momentum to make the tactile movement noticeable through the skin 25 of the device.

In a preferred embodiment, the device is designed to be used in an orientation where the direction to the rescuers hands is upward, so that the core does not need any springs or similar structure to fall back in place after being moved. Gravity will simply lead it back into its starting position at the support 24, defined by the device housing, before the next compression and possible emission of an electronic pulse. Other solutions, such as springs, may be contemplated under certain conditions, but resulting in a more complicated tactile unit.

Also, in an embodiment without the skin over the hole 21, protruding features or similar may be provided on the magnet or coil housing to stop the magnet from falling out of the device.

Different coils can be designed to dimension, design and wire. The following parameters are important in the design of the coil:
  Size
  Electrical power
  Complexity
  Price
  Reliability A coil with low resistance and high inductance is desirable for many applications. High inductance is desirable since high inductance is synonymous with high field strength ($\Phi$). To get higher inductance more windings are needed. To get lower resistance, the wire must have a higher cross-sectional area. This will make the coil bigger with respect to the inductance. The coil former should be made as big as possible (20×13 mm is a practical dimension for use in a CPR sensor), and the choice of number of windings and wire dimension should be done based on the coil former size. This means that the coil is preferably as optimal as possible due to the limitations set by the design. The drive circuit presented in FIG. 15 will enable more flexibility with respect to the choice of wire gauge and number of windings.

In an example embodiment, the coil former 26 (see FIG. 10b) has a total height of 13 mm. The wire is only wound in a 6 mm high section of the coil former the rest of the coil former is used as guidance for the magnet.

The bottom end of the coil may be closed off by a lid (not shown). The center piece of the lid is 8 mm in diameter in a practical embodiment and protrudes into the air gap of the coil forming the support 24 for the magnet 23. On top of the center piece a piece of 1 mm thick rubber is attached. The rubber will ensure that when the permanent magnet returns to its start position, it will not make audible noise. The center piece will also provide the offset of the magnet needed to get "ejecting forces" as described above. The wire used to wind the coil in this example embodiment is a standard lacquer insulated copper wire, 0.15-0.18 mm thick.

The permanent magnet which has been used in the example embodiment is a powerful neodymium (N35), rare earth magnet. Magnets of this type have become widely used in number devices, such as speakers in mobile phones. These magnets have a powerful field compared to the mass, but they are mechanically fragile and loose their magnetism at temperatures above 80 degrees C. Other magnets may be used depending on the required specifications.

On top of the magnet 23 there preferably is a dome to make the snap more "focused", as is shown on the top of the magnet illustrated in FIG. 10b. The magnet is preferably made in one piece, but certain features, such as the dome, may be made separately, depending on the required characteristics as shown in 27 and 27a, where the dome is made of is iron.

Figure 14:
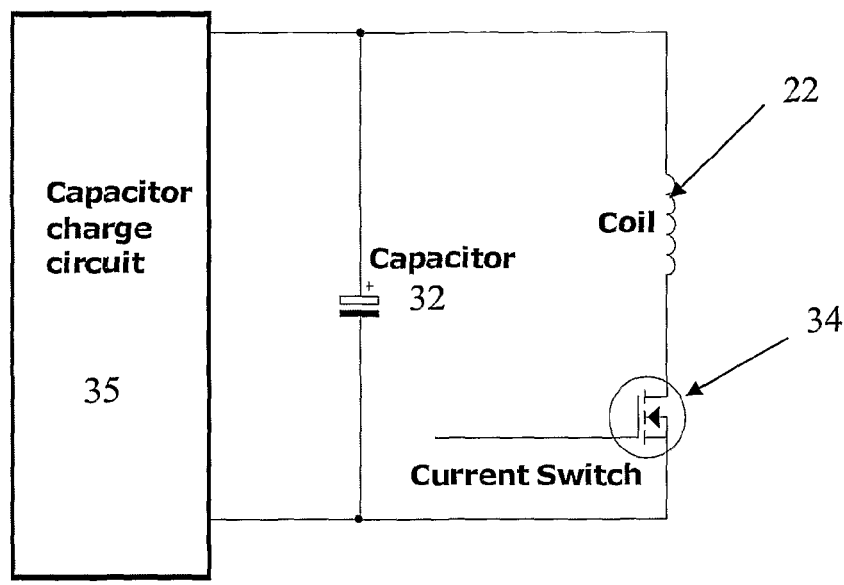
FIG. 14 is a schematic diagram of circuitry suitable for use with the feedback unit in accordance with an embodiment of the present invention.
Figure 15:
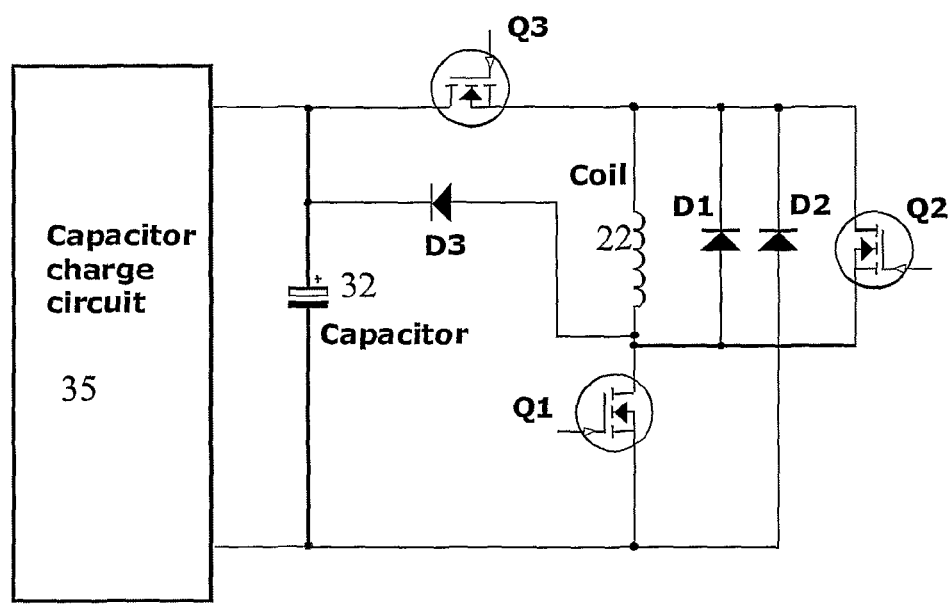
FIG. 15 is a schematic diagram of alternative circuitry suitable for use with the feedback unit in accordance with an embodiment of the present invention.

In FIGS. 14 and 15, the electronic circuitry coupled to the coil 22 is described. The circuitry and thus the operation of the feedback actuator is controlled by the processing means. A capacitor charge circuit 35 will charge the capacitor 32 efficiently from batteries. The batteries will typically have a low voltage (3-5V), but the capacitor should be charged to a higher voltage (20-50V typically). This will produce a more powerful field in the coil 22 and thus accelerate the magnet 23 positioned therein more forcefully when the feedback device is activated. The current switch 34 will turn on the current through the coil 22 at the correct time. When the magnet 23 has been accelerated past the coil gap, the current switch will turn off.

A more sophisticated circuit is illustrated in FIG. 15, where some components have been added to improve the energy efficiency of the circuit. In FIG. 15 the capacitor 32 is charged by the capacitor charge circuit 35. At the correct point in time switches Q1 and Q3 are turned on (switch Q2 is off). Current will build in the coil. When the current reaches maximum current; which is synonymous with maximum field strength in the coil gap; Q1 and Q3 are turned off. Immediate after this, switch Q2 is turned on. Current will now continue to flow through the coil and Q2. The current will fall as energy is consumed either by the resistivity of the coil or by energy transfer to the permanent magnet 23 when it is accelerated by the field in the coil 22.

When the permanent magnet has moved out of the coil 22 switch Q2 will turn off; the remaining energy in the coil will flow back to the capacitor through D2 and D3. The diode D1 is adapted to prevent transients during the switching process.

The key benefits of this circuit are:

Energy is only drawn from the capacitor until maximum field is established.

If the coil has low resistance the energy of the coil will be transferred to mechanical motion of the magnet.

Remaining energy in the coil is delivered back to the capacitor.

The capacitor charge circuit 35 will be designed to fully charge the capacitor 32 between each compression of the chest. At the same time the charge circuit will be designed to draw current from the batteries at an almost constant rate to avoid loss of battery power due to high peak currents.

The invention claimed is:

1. A system for monitoring parameters during cardiopulmonary resuscitation, comprising:
    a compression unit operable to produce an output corresponding to compressions performed on a subject;
    a ventilation sensor operable to produce a ventilation output corresponding to ventilations performed on the subject;
    a processor connected to the compression sensor and ventilation sensor and programmed to compare the compression output and the ventilation output with respective reference ranges, and, if at least one of the compression output and ventilation output deviate from the respective reference ranges, provide an indication of the deviation; and
    wherein in the case of more than one of the compression output and ventilation output deviating from the respective reference ranges, the processor is programmed to provide a sequence of indications in prioritized order based at least in part on which of the more than one of the compression output and ventilation output is more medically critical at that stage of cardiopulmonary resuscitation.

2. The system of claim 1, further comprising a feedback unit operable to provide the indication of the deviation in the form of at least one of an audible, visible, and tactile output.

3. The system of claim 2, wherein the feedback unit comprises a coil wound around a central hole and a magnetic core arranged moveably in the central hole of the coil, the coil being connected to an electric power supply selectively switched on and off in order to induce movement of the magnetic core.

4. The system of claim 1, wherein the compression unit, feedback unit and the processor are integrated in a housing.

5. The system of claim 1, wherein the ventilation sensor measures at least one of ventilation rate, tidal volume, and inflation time.

6. The system of claim 5, wherein the ventilation sensor includes a pressure sensor.

7. The system of claim 1, wherein the compression unit is operable to measure at least one of compression rate and compression depth.

8. The system of claim 1, wherein the compression unit includes at least one of a force sensor and an accelerometer and wherein the compression output corresponds to an output from at least one of the force sensor and the accelerometer.

9. The system of claim 1, wherein the processor and at least one of the compression unit and ventilation sensor are integrated in a housing.

10. The system of claim 1, wherein the processor is programmed to prioritize the sequence of indications by comparing the compression output and ventilation output corresponding to the sequence of indications with a priority list stored in the processing means.

11. The system of claim 1, wherein the subject is a manikin.

12. The system of claim 1, wherein the prioritized order is based, at least in part, on at least one of the compression output and the ventilation output.

13. A method for monitoring parameters during cardiopulmonary resuscitation of a subject, the method comprising:
    measuring compression;
    measuring ventilation;
    comparing the compression and ventilation measurements with respective reference ranges, and if at least one of the compression and ventilation measurements deviate from the respective reference range, providing an indication of the deviation,
    and in the case of more than one of the compression and ventilation measurements deviating from the respective reference ranges, providing a sequence of indications in a prioritized order, wherein the prioritized order is determined by the respective deviations from the respective reference ranges for the more than one of the compression and ventilation measurements and further based on which of the compression and ventilation acts of the cardiopulmonary resuscitation are more medically critical.

14. The method of claim 13, wherein providing the indication of the deviation comprises giving an audible, visible, or tactile indication.

15. The method of claim 13, wherein measuring ventilation comprises measuring at least one of ventilation rate, tidal volume and inflation time.

16. The method of claim 13, wherein measuring ventilation comprises measuring airflow within an airway adapter in fluid communication with the airway of the subject.

17. The method of claim 13, wherein measuring compression comprises measuring at least one of compression rate and compression depth.

18. The method of claim 13, wherein the measuring compression is performed by a compression unit contacting the chest of the subject.

19. The method of claim 13, wherein the subject is a manikin.

20. The method of claim 13 wherein providing the sequence of indications includes comparing the at least one of the compression measurement and ventilation measurement corresponding to the deviation from the respective reference ranges to a priority list.

21. A compression unit positionable on a subject's chest comprising:
    a compression sensor operable to produce a compression output corresponding to a compression depth;
    a processor connected to the compression sensor and programmed to compare the compression output with a reference range and, if the compression output falls within the reference range, provide an indication signal; and
    a feedback unit connected to the processor for providing a tactile output corresponding to the indication signal, wherein the tactile output is created when an actuated magnetic core displaces and taps a user of the compression unit, wherein the tap of the magnetic core on the user is configured to inform the user to adjust compressions.

22. The compression unit of claim 21, wherein the feedback unit comprises a coil defining a central hole, and the magnetic core movably disposed in the central hole, the coil being coupled to the processor and the processor being programmed to provide the indication signal by coupling the coil to an electric power supply.

23. The device of claim 21, wherein the compression sensor, processor, and feedback unit are mounted to a housing and wherein the feedback unit is disposed off-center to the housing.

24. The device of claim 23, wherein the housing comprises a cover having a recess positioned directly over the feedback unit.

25. The device of claim 21, wherein the compression sensor measures compression rate.

26. The device of claim 21, further comprising a connector for coupling the processor to at least one of a ventilation sensor and a second feedback unit.

27. The device of claim 21, wherein the compression sensor includes at least one of a force sensor and an accelerometer and wherein the compression output corresponds to an output from at least one of the force sensor and the accelerometer.

* * * * *